(12) United States Patent
Knerr

(10) Patent No.: US 6,689,393 B1
(45) Date of Patent: Feb. 10, 2004

(54) SOLUTION, IN PARTICULAR FOR HEMODIALYSIS OR PERITONEAL DIALYSIS AND A METHOD OF PREPARING SAME

(75) Inventor: Thomas Knerr, St. Wendel (DE)

(73) Assignee: Fresenius Medical Care Deutschland, Bad Homburg (DE)

( * ) Notice: Subject to any disclaimer, the term of this patent is extended or adjusted under 35 U.S.C. 154(b) by 0 days.

(21) Appl. No.: 09/533,289

(22) Filed: Mar. 22, 2000

(30) Foreign Application Priority Data

Mar. 22, 1999 (DE) .......................... 199 12 850

(51) Int. Cl.$^7$ ..................... A61K 33/00; A61K 31/19; A61K 31/70; A61J 1/10; A61M 37/00
(52) U.S. Cl. ..................... 424/682; 424/666; 424/677; 424/678; 424/679; 424/680; 424/681; 424/686; 424/717; 514/23; 514/557; 514/574; 514/722; 604/82; 604/408; 604/410
(58) Field of Search ........................ 424/44, 666, 677, 424/678, 679, 680, 681, 682, 686, 717; 514/25, 557, 574, 722, 23; 604/82, 408, 410

(56) References Cited

U.S. PATENT DOCUMENTS

| 4,489,535 | A | * | 12/1984 | Veltman ..................... 53/431 |
| 4,630,727 | A | | 12/1986 | Feriani et al. ............... 206/221 |
| 5,071,558 | A | | 12/1991 | Itoh .......................... 210/542 |
| 5,296,242 | A | | 3/1994 | Zander ....................... 424/715 |
| 5,827,820 | A | | 10/1998 | duMoulin et al. .............. 514/2 |
| 5,871,477 | A | * | 2/1999 | Isono et al. .................. 604/410 |
| 5,925,011 | A | * | 7/1999 | Faict et al. ................... 604/29 |
| 5,945,129 | A | | 8/1999 | Knerr et al. ................. 424/676 |

FOREIGN PATENT DOCUMENTS

| DE | 40 39 471 | 6/1992 |
| DE | 41 22 754 | 1/1993 |
| DE | 42 11 455 | 12/1993 |
| DE | 42 11 455 C1 | 12/1993 |
| DE | 196 54 746 A1 | 7/1998 |
| EP | 0 076 355 | 4/1983 |
| EP | 402 505 A1 | 12/1989 |
| EP | 0 402 505 | 12/1990 |
| EP | 0 564 672 | 10/1993 |
| EP | 0 613 688 A1 | 9/1994 |
| EP | 613 688 A1 | 9/1994 |
| JP | 8-131542 | 5/1996 |
| JP | 09087182 | 3/1997 |
| JP | 11070166 | 3/1999 |
| WO | WO 91/08008 | 6/1991 |
| WO | WO 93/08920 | 5/1993 |
| WO | WO 93/09820 | 5/1993 |
| WO | WO 93/19792 | 10/1993 |
| WO | WO 96/01118 | 1/1996 |
| WO | WO 97/05852 | 2/1997 |
| WO | WO 99/09953 | 3/1999 |
| WO | WO 00 57833 | 10/2000 |

OTHER PUBLICATIONS

Database CAPLUS Online! Chemical Abstracts Service, Columbus, Ohio, US; Trezeciak, Marzenna et al.: "Effect of the Electrolyte Components of Peritoneal Dialysis Solutions on Stability of Glucose" Database Accession No. 1990:25482, XP002225451.

Thomas J. Comstock, "Renal Dialysis—Chapter 31", Applied Therapeutics—The clinical use of drugs (sixth ed.), edited by Young and Koda–Kimble, pp. 31–1 to 31–15 (1995).

H.E. Franz, "Blood Purification Methods," published by Georg Thieme Verlag, Stuttgart, NY, 1990, pp.479–492.

* cited by examiner

Primary Examiner—Thurman K. Page
Assistant Examiner—Frank Choi
(74) Attorney, Agent, or Firm—Kenyon & Kenyon

(57) ABSTRACT

A solution, in particular for hemodialysis or peritoneal dialysis that permits attaining a desired glucose concentration without affecting the concentrations of other components in the solution. The solution consists of at least three individual solutions that are combined and administered after heat sterilization. The first solution contains calcium ions, electrolyte salts and optionally glucose in a concentration of 0–1000 mM and is acidified to a pH of less than 4.0 with a physiologically tolerable acid. The second solution contains glucose in a concentration different from that of the first solution and the remaining components of the first solution in the same concentration. The third solution contains a buffer in the physiological range. Also provided is a method of preparing a solution according to the invention, where the desired mixing ratio of the separate solutions is automatically established by a dialysis machine or peritoneal dialysis cycler.

29 Claims, No Drawings

SOLUTION, IN PARTICULAR FOR HEMODIALYSIS OR PERITONEAL DIALYSIS AND A METHOD OF PREPARING SAME

FIELD OF THE INVENTION

The present invention relates to a solution, in particular for hemodialysis or peritoneal dialysis and a method for preparing same.

BACKGROUND OF THE INVENTION

The most important functional components of hemodialysis or peritoneal dialysis solutions are electrolytes which preferably include calcium ions, sodium ions, magnesium ions and chloride ions, a buffer system, and a suitable osmotic medium.

A bicarbonate buffer having the advantage of good physiological tolerability is generally used as the buffer system, but depending on the pH of the solution, it is partially in carbonate form in an alkaline medium and in equilibrium with $CO_2$ in an acidic range. In addition to bicarbonate, other buffers can also be used, providing they have sufficient buffering effect in the physiological pH range of approximately 7. Suitable buffers include lactate and pyruvate, which can be degraded easily to bicarbonate in the body.

The osmotic medium is usually glucose, which is tolerated well in the desired osmolarity range.

One important problem in preparing a dialysis solution containing the functional components is that bicarbonate and calcium must usually be stored separately to prevent formation of an insoluble calcium carbonate precipitate. Although such a precipitate can be prevented in an acidic range, there is the problem of the bicarbonate-$CO_2$ equilibrium being on the $CO_2$ side in the acidic range. The relatively high resulting $CO_2$ partial pressure requires a bag film with a large, i.e., effective, $CO_2$ barrier.

If glucose is used as the osmotic medium, glucose may react with the other components of the solution during heat sterilization of the solution, and degradation products which might have a harmful effect on the body may be formed. In particular the reaction of glucose with lactate, which is also used as a buffer, bears mentioning.

Therefore, it is known from International Patent WO 93/09820, for example, that glucose and the other components of the dialysis solution may be sent for heat sterilization separately. Said patent discloses a dual-chamber vessel where all the important components of the dialysis solution except for glucose are accommodated in a large compartment, while the glucose or glucose-like components are stored in a second compartment. This makes it possible to effectively prevent the formation of glucose degradation products during heat sterilization. After heat sterilization, the components of the two compartments are mixed and the solution is used for hemodialysis or peritoneal dialysis in a known manner.

European Patent 613 688 A1 describes a dialysis fluid consisting of multiple individual concentrates. A uniform, standardized basic concentrate and an individually selected additive concentrate are provided. The basic concentrate contains sodium chloride and sodium bicarbonate. The additive concentrate preferably contains the other electrolytes and glucose. In addition to the separation of glucose from the buffer system and the associated reduction in formation of unwanted degradation products, this yields the advantage that the composition of the dialysis solution can be adapted to the prevailing needs of the patients through the individually selected additive concentrate. This makes it possible to administer potassium salts, calcium salts and magnesium salts as well as glucose in individually adjusted doses.

European Patent 402 505 A1 discloses a method and a device for continuous cyclic peritoneal dialysis, where a glucose pump is connected to an inlet line for a dialysis solution leading to the patient. Depending on the delivery head of the glucose pump, the glucose concentration in the peritoneal dialysis solution supplied to the patient may be adjusted. The glucose content in the solution to be administered is adjusted on the basis of the quantity of ultrafiltrate taken from the patient.

The previously known methods of preparing dialysis solutions have the disadvantage that although different concentrations or profiles of components, in particular glucose, can be achieved in the finished mixture by combining two individual solutions, mixing the individual solutions always leads to a corresponding change in the concentrations of the other components as well. For example, if glucose is added in the method known from European Patent 402,505 A1, this also results in changes in the concentrations of the other components of the dialysis solution, e.g., the electrolytes or the pH, depending on the mixing ratio.

OBJECTS OF THE INVENTION

Therefore, the object of the present invention is to provide a solution, in particular for hemodialysis or peritoneal dialysis, and a method of preparing same, by means of which the glucose concentration can be varied as desired without influencing the concentration of the other components.

This object is achieved by a solution consisting of at least three individual solutions which are combined and administered after heat sterilization, where the first individual solution contains calcium ions, electrolyte salts and optionally glucose in concentrations of 0–1000 mM and is acidified to a pH below 4.0 with a physiologically tolerable and effective acid, where the second individual solution contains glucose in a different concentration and all the other components of the first individual solution in the same concentration, i.e., as in the first individual solution, and where the third individual solution contains a buffer in the physiological range.

Such a solution yields the advantage that the glucose concentration can be varied as desired according to the mixing ratio of the first and second individual solutions without affecting the concentrations of the other components.

Furthermore, the solution according to the present invention has the advantage that the calcium ions and the bicarbonate are accommodated in separate compartments, thus avoiding the disadvantages of simultaneous presence of both components as described above.

Sterilization of the individual solutions according to the present invention is not problematical, as it has been found that glucose can be sterilized without significant problem at a pH of less than 4.0. Fewer degradation products of glucose are formed due to the low pH. In this way, it is possible to prevent or greatly reduce infusion pain in dialysis patients due to the low concentration of degradation products, i.e., the dialysis solution prepared from the individual solutions according to the present invention has a high biocompatibility. The buffer used in the third individual solution has a pH of approximately 7.2 to 7.4. The buffer solution may consist of a bicarbonate solution, for example, with the bicarbonate content in the mixed solution being below 40 mM. The buffer is preferably prepared from $HCO_3^-$ and a salt of a weak acid.

It is especially advantageous if the third individual solution contains bicarbonate in a maximum concentration of 10 mmol/L. This makes it possible to minimize the $CO_2$ pressure inside the respective compartment so that no special $CO_2$ barrier need be provided to prevent the escape of $CO_2$. Instead, use of a normal polyolefin film or a normal PVC film is sufficient to keep the bicarbonate concentration constant. The buffer of the third individual solution can contain solely bicarbonate. It is likewise possible for the buffer to also contain a salt of a weak acid, preferably lactate, whose buffer capacity is supported by the bicarbonate in the combined buffer.

In another embodiment of the present invention, the second individual solution may not contain any glucose. In this case, the glucose is provided only in the first individual solution and is metered by mixing this solution with the second individual solution in the desired concentration. It is of course also possible for the second individual solution to also contain glucose, but in a different concentration than the first individual solution.

It is especially advantageous if the first and second individual solutions have a pH of 2.8 to 4.0, preferably a pH of 3.7, and if the third individual solution has a pH of 8.5 to 9.0, so that a pH of 6.8 to 7.4 is established in the finished solution with a mixture having a ratio of five parts of the third individual solution to 13 parts of any desired mixture of the first and second individual solutions.

In another embodiment of the present invention, calcium ions, sodium ions, magnesium ions, excess $H^+$ ions, chloride ions and glucose are present in the first and second individual solutions.

The third individual solution may contain sodium, ions as well as one or more salts of weak acids. Such salts may include pyruvate ions, alpha-ketoglutarate ions, lactate ions and bicarbonate ions.

It is especially advantageous if the physiologically tolerable acid is hydrochloric acid.

DETAILED DESCRIPTION OF THE PREFERRED EMBODIMENT

In a preferred embodiment of the present invention, the first and second individual solutions include the following ingredients:

| sodium: | 120 to 140 mmol/L, preferably 133 mmol/L |
|---|---|
| calcium: | 1–3 mmol/L, preferably 1.7 or 2.4 mmol/L |
| magnesium: | 0.5 to 1.0 mmol/L, preferably 0.7 mmol/L |
| excess $H^+$: | 0.9 to 1.1 mmol/L, preferably 1.0 mmol/L |
| chloride: | 130 to 150 mmol/L, preferably 140 mmol/L |

The first individual solution also contains glucose in a concentration of about 200 to 1000 mmol/L, preferably 500 mmol/L, and the second individual solution does not contain any glucose.

The third individual solution advantageously has the following ingredients:

| sodium: | 120 to 140 mmol/L, preferably 136 mmol/L |
|---|---|
| lactate: | 100 to 140 mmol/L, preferably 126 mmol/L |
| bicarbonate: | 5 to 10 mmol/L, preferably 10 mmol/L |

Moreover, the tolerable concentrations depend on the mixing ratio of the sum of the first and second solutions to the third individual solution. In the preferred embodiment, five parts of the first individual solution, eight parts of the second individual solution and five parts of the third individual solution are combined.

In another embodiment of the present invention, the minimum of three individual solutions are stored in a multichambered bag. The multichambered bag may be designed as a plastic bag having one chamber for each of the individual solutions.

It is especially advantageous if the third individual solution contains the salt of a weak acid. The weak acid advantageously has a pKa value of <5.

The present invention also concerns a method of preparing a solution according to the present invention, where the desired mixing ratio is established automatically by the dialysis machine or the peritoneal dialysis cycler.

Additional advantages and details of the present invention are explained in greater detail on the basis of one embodiment.

To prepare the first and second individual solutions, 7.784 g sodium chloride, 0.3557 g calcium chloride.$2H_2O$, 0.1407 g magnesium chloride.$6H_2O$ and 0.130 mL 25% hydrochloric acid are dissolved in water and topped off to 1000 mL. In addition, 99 g glucose monohydrate is added to one of the two solutions. The necessary correction of the pH to <4.0 can be effected by adding or omitting 25% hydrochloric acid or sodium hydroxide. Both solutions are filtered through membrane prefilters and then through sterile membrane filters into a cooling tank. After inspecting the batch and releasing the solutions, they are packaged in a multichambered laminated film bag and sealed with connectors. The dry bag is then repackaged in an outer bag and then heat sterilized at 121 degrees C.

To prepare the third individual solution, 28.25 g sodium lactate as a 50% solution and 0.840 g sodium bicarbonate are dissolved while stirring slowly in 977 mL water for injection cooled to 12 to 14 degrees C. The temperature of the solution should not exceed 20 degrees C. during the batching and storage time. The solution is then filtered through a membrane prefilter and a sterile membrane filter into a cooling tank. After inspection of the batch and release of the solution, it is packaged in the multichambered bag and sealed with connectors. The dry bag is transferred to an outer bag and then sterilized at 121 degrees C.

The first and second individual solutions are mixed together in a desired ratio for use. Mixing may be constant over time or it may be varied over time to achieve a concentration gradient. The mixture of the first and second individual solutions is mixed with the third individual solution in a ratio of 13:5.

All the individual solutions are in separate compartments which can form a connection to one another or their outlets may open into a common line or mixing chamber. A resealable flow control element is provided in this connection/outlet line, so the amount of individual solutions can be adjusted and varied individually during use. A flow control element may be, for example, a roll clamp or an occluding pump.

What is claimed is:
1. A dialysis solution comprising:
(a) a first individual solution comprising calcium ions, electrolyte salts and optionally glucose in a concentration of not more than 1000 mM;
(b) a second individual solution optionally comprising glucose in a concentration different from that of the first individual solution, and the remaining components in the same concentration as that of the first individual solution; and
(c) a third individual solution comprising a buffer;
wherein at least one of the first individual solution and the second individual solution contains glucose and wherein each of the first and second individual solutions which comprise glucose is acidified to a pH lower than 3.0;
wherein the first, second and third solutions are combined to form a combined solution having a total glucose so as to be administered, wherein the combined solution is such that the glucose will not be substantially degraded upon being heat sterilized; and
wherein by varying the volume of the first solution with respect to the volume of the second solution, the total glucose concentration can be altered, while the concentrations of the remaining components having identical concentrations in the first and second individual solutions remain the same.

2. The solution of claim 1, wherein the solution is selected from the group consisting of hemodialysis or peritoneal dialysis solutions.

3. The solution of claim 1, wherein the first and second individual solutions are acidified with a physiologically tolerable acid.

4. The solution of claim 3, wherein the physiologically tolerable acid is hydrochloric acid.

5. The solution of claim 1, wherein the first individual solution is acidified to a pH of less than about 4.0.

6. The solution of claim 1, wherein the buffer is physiologically acceptable.

7. The solution of claim 1, wherein the buffer is bicarbonate.

8. The solution of claim 1, wherein the second individual solution contains no glucose.

9. The solution of claim 1, wherein a pH of about 6.8 to 7.4 is established in the solution when the first, second and third individual solutions are mixed.

10. The solution of claim 1, wherein the first and second individual solutions have a pH of about 2.8 to about 4.0 and the third individual solution has a pH of about 8.5 to about 9.0, and wherein a pH of about 6.8 to about 7.4 is established in the solution when five parts of the third individual solution is combined with 13 parts of a mixture of the first and second individual solutions.

11. The solution of claim 1, wherein the first and second individual solutions have a pH of 3.7.

12. The solution of claim 1, wherein the first and second individual solutions further comprise sodium ions, magnesium ions, excess $H^+$ ions, and chloride ions.

13. The solution of claim 1, wherein the third individual solution contains sodium ions and one or more salts of weak acids.

14. The solution of claim 13, wherein the weak acids have a pKa value of <5.

15. The solution of claim 13, wherein the salts of weak acids are selected from the group consisting of pyruvate ions, alpha-ketoglutarate ions, lactate ions and bicarbonate ions.

16. The solution of claim 1, wherein the first and second individual solutions include:

| sodium: | 120–140 mmol/L; |
|---|---|
| calcium: | 1–3 mmol/L; |
| magnesium: | 0.5–1.0 mmol/L; |
| excess $H^+$: | 0.9–1.1 mmol/L; |
| chloride: | 130–150 mmol/L; and | wherein the first individual solution contains about 200 to about 1000 mmol/L glucose.

17. The solution of claim 1, wherein the first and second individual solutions include:

| sodium: | 133 mmol/L; |
|---|---|
| calcium: | 1.7 to 2.4 mmol/L; |
| magnesium: | .7 mmol/L; |
| excess $H^+$: | 1.0 mmol/L; |
| chloride: | 140 mmol/L; and | wherein the first individual solution contains 500 mmol/L glucose.

18. The solution claim 1, wherein the third individual solution includes:

| sodium: | 120–140 mmol/L |
|---|---|
| lactate: | 100–140 mmol/L |
| bicarbonate: | 5–10 mmol/L. |

19. The solution of claim 1, wherein the third individual solution includes:

| sodium: | 136 mmol/L |
|---|---|
| lactate: | 126 mmol/L |
| bicarbonate: | 10 mmol/L. |

20. The solution of claim 1, wherein the first, second and third individual solutions are stored in a multichambered bag.

21. The dialysis solution of claim 1, wherein the first, second and third solutions are administered after heat sterilization.

22. A dialysis solution comprising:
(a) a first individual solution comprising calcium ions and electrolyte salts;
(b) a second individual solution comprising glucose in addition to calcium ions and electrolyte salts in the same concentration as that of the first individual solution, the second individual solution being acidified to a pH lower than 3.0; and
(c) a third individual solution comprising a buffer;
wherein the first solution does not contain glucose; and
wherein the first, second and third solutions are combined to form a combined solution having a total glucose concentration, so as to be administered, wherein the combined solution is such that the glucose will not be substantially degraded upon being heat sterilized; and
wherein the total glucose concentration can be altered while the concentrations of other components having identical concentrations in the first and second individual solutions remain the same by varying the volume of the first solution and the second solution.

23. The dialysis solution of claim 22, wherein the first, second and third solutions are administered after heat sterilization.

24. A dialysis solution comprising:

(a) a first individual solution comprising:

| | |
|---|---|
| sodium: | 120–140 mmol/L, |
| calcium: | 1–3 mmol/L, |
| magnesium: | 0.5–1.0 mmol/L, |
| excess $H^+$: | 0.9–1.1 mmol/L, |
| chloride: | 130–150 mmol/L, |
| glucose: | not more than 1000 mmol/L; |

(b) a second individual solution comprising

| | |
|---|---|
| sodium: | 120–140 mmol/L, |
| calcium: | 1–3 mmol/L, |
| magnesium: | 0.5–1.0 mmol/L, |
| excess $H^+$: | 0.9–1.1 mmol/L, |
| chloride: | 130–150 mmol/L, |
| glucose: | not more than 1000 mmol/L, | wherein the concentration of glucose in the second individual solution is different from the glucose concentration in the first individual solution, and wherein at least one of the first individual solution and the second individual solution contains glucose, wherein each of the first and second individual solutions that comprise glucose is acidified to a pH lower than 3.0, and (c) a third individual solution comprising

| | |
|---|---|
| sodium: | 120–140 mmol/L |
| lactate: | 100–140 mmol/L |
| bicarbonate: | 5–10 mmol/L; | wherein the first, second and third individual solutions are combined and the dialysis solution has a pH of about 6.8 to about 7.4, and wherein the solutions are such that the glucose will not be substantially degraded upon being heat sterilized.

25. The solution of claim 24, wherein the first and second individual solutions have a pH of about 2.8 to about 4.0.

26. The solution of claim 24, wherein the third individual solution has a pH of about 8.5 to about 9.0.

27. The dialysis solution of claim 24, wherein the first, second and third individual solutions are combined after heat sterilization.

28. A method of preparing a dialysis solution in a dialysis unit comprising:

(1) providing a first individual solution comprising calcium ions, electrolyte salts and optionally glucose;

(2) providing a second individual solution comprising optionally glucose in a concentration different from that of the first individual solution and the remaining components in the same concentration as that of the first individual solution, wherein at least one of the first individual solution and the second individual solution contains glucose and wherein each of the first and the second individual solutions which comprise glucose is acidified to a pH lower than 3.0;

(3) providing a third individual solution comprising a buffer;

(4) heat sterilizing the first, second and third individual solutions; and (5) combining the first, second and third individual solutions in the dialysis unit;

wherein the mixing ratio of the individual solutions is automatically established by the dialysis unit to establish a pH in the dialysis solution of about 6.8 to about 7.4, and wherein the solutions are such that the glucose will not be substantially degraded upon being heat sterilized.

29. The method of claim 28, wherein the dialysis unit is selected from the group consisting of a dialysis machine or a peritoneal dialysis cycler.

* * * * *

UNITED STATES PATENT AND TRADEMARK OFFICE
CERTIFICATE OF CORRECTION

PATENT NO.    : 6,689,393 B1  
DATED         : February 10, 2004  
INVENTOR(S)   : Knerr It is certified that error appears in the above-identified patent and that said Letters Patent is hereby corrected as shown below:

Column 4,  
Line 31, change "magnesium chloride.6H$_2$O" to -- magnesium chloride·6H$_2$O --;

Column 5,  
Lines 18-21, delete "having a total glucose so as to be administered, wherein the combined solution is such that the glucose with not be substantially degraded upon being heat sterilized";  
Line 48, change "to about" to -- up to but not including --;

Column 6,  
Lines 11-12, change "to about" to -- not more than --;  
Lines 59-62, delete "having a total glucose so as to be administered, wherein the combined solution is such that the glucose with not be substantially degraded upon being heat sterilized";

Column 8,  
Lines 1-3 and 35-37, change "7.4, and wherein the solutions are such that the glucose will not be substantially degraded upon being heat sterilized." to -- 7.4. --;  
Line 5, change "to about" to -- up to but not including --;

Signed and Sealed this

First Day of February, 2005

JON W. DUDAS  
*Director of the United States Patent and Trademark Office*